United States Patent [19]  
Dodd

[11] 4,381,413  
[45] Apr. 26, 1983

[54] PROCESS FOR CONVERTING ANISOLES TO ORTHO-METHYLATED PHENOLIC PRODUCTS

[75] Inventor: John R. Dodd, Ponca City, Okla.

[73] Assignee: Conoco Inc., Ponca City, Okla.

[21] Appl. No.: 286,501

[22] Filed: Jul. 24, 1981

[51] Int. Cl.$^3$ .............................................. C07C 39/04
[52] U.S. Cl. ...................................... 568/716; 568/806
[58] Field of Search ................ 568/716, 806, 780, 805

[56] References Cited

U.S. PATENT DOCUMENTS

| | | | |
|---|---|---|---|
| 2,289,886 | 7/1942 | Schmerling | 568/716 |
| 2,697,732 | 12/1954 | Mavity | 568/805 |
| 3,247,263 | 4/1966 | Weiderhammer | 568/806 |
| 4,278,816 | 7/1981 | Shim | 568/716 |
| 4,283,572 | 8/1981 | Klicker | 568/780 |

FOREIGN PATENT DOCUMENTS 600839 4/1948 United Kingdom ................ 568/806

OTHER PUBLICATIONS

Kolka et al., "J. Organic Chem.", vol. 22, (1957), pp. 642–646.
Bowman et al., "J. Amer. Chem. Soc.", vol. 79, (1957), pp. 87–92.
Wagner et al., "Synthetic Organic Chem.", (1953), pp. 171–172, pub. John Wiley & Son, New York.
Obolentsey, "Chem. Abstract", vol. 41, (1947), pp. 5477–5478.

*Primary Examiner*—Werren B. Lone
*Attorney, Agent, or Firm*—Robin M. Dowling

[57] ABSTRACT

A process for converting anisoles to ortho-methylated phenolic products in high selectivity is disclosed. The process comprises passing methoxybenzene, o-methylmethoxybenzene, 2,6-dimethylmethoxybenzene, or mixtures thereof, over gamma-alumina in the presence of an effective amount of water at a temperature in the range of about 225° to about 295° C.

9 Claims, No Drawings

PROCESS FOR CONVERTING ANISOLES TO ORTHO-METHYLATED PHENOLIC PRODUCTS

FIELD OF THE INVENTION

The invention is in the general field of preparing ortho-methylated phenolic products from anisoles (e.g. methoxybenzene).

GENERAL BACKGROUND

Methylated phenolic products have many uses. For example, 2,6-xylenol is useful in polymer synthesis. It is the primary monomer for producing polyphenylene oxide, which is an important engineering plastic.

o-Cresol is a valuable intermediate in herbicide synthesis, especially for making 2-methyl-4-chlorophenoxyacetic acid and 2-methyl-4-chlorophenoxypropionic acid. Both of these compounds are widely used as herbicides in Europe.

Blends of such cresylics as o-cresol and 2,6-xylenol are useful for a variety of applications, including use as disinfectants, use as solvents for the magnet wire industry, and use as metal cleaners (degreasers, paint strippers, et cetera).

The conversion of anisoles to methylated phenolic products over solid catalysts such as gamma-alumina is known. The vapor phase conversion of anisoles, such as methoxybenzene, o-methylmethoxybenzene, and 2,6-dimethylmethoxybenzene, in general yields a wide variety of isomeric cresols and xylenols. It would be highly desirable to have a process which provides a high selectivity of o-cresol and/or 2,6-xylenol in the product mixture. I have developed a process which provides the desired high selectivity of o-cresol and/or 2,6-xylenol in the product mixture.

BRIEF SUMMARY OF THE INVENTION

Briefly stated, the present invention is directed to a process for converting a feedstock comprising methoxybenzene, o-methylmethoxybenzene, 2,6-dimethylmethoxybenzene, or mixtures thereof, to ortho-methylated phenolic products, such as o-cresol and 2,6-xylenol, in high selectivity wherein the process comprises passing the feedstock in vapor phase over an effective amount of gamma-alumina in the presence of an effective amount of water at a temperature in the range of about 225° to 295° C.

DETAILED DESCRIPTION

The feedstock used in my process comprises methoxybenzene (anisole), o-methylmethoxybenzene, and 2,6-dimethylmethoxybenzene. The materials can be used individually or in any combination of mixtures.

My process uses gamma-alumina. Generally any alumina which has been calcined at about 470° to about 870° C. for at least one hour, to provide gamma-alumina, is suitable. The preferred alumina is one that has been calcined at 500° to 650° C. for about 1 to about 3 hours.

Suitable alumina has a surface area in the range of about 75 to about 350 m²/g. Preferably, the surface area is in the range of about 150 to about 200 m²/g.

The alumina can be in a variety of shapes and sizes, e.g. spheres, pellets, tablets.

As implied in the foregoing the feedstock and water are passed in the vapor phase over the gamma-alumina catalyst in a suitable reaction vessel (e.g. a tube or cylinder).

The amount of water used, based on the feedstock, as weight percent is as follows:

|  | Suitable | Preferred |
|---|---|---|
| Water (based on feedstock), about | 0.5–10 | 1–4 |

The amount of gamma-alumina catalyst used can be expressed as follows:

$$\frac{\text{weight of feedstock per hour}}{\text{weight of catalyst}}$$

On this basis the suitable and preferred amounts of catalyst are:

|  | Suitable | Preferred |
|---|---|---|
| about | 0.5–2.5 hr$^{-1}$ | 0.8–1.5 hr$^{-1}$ |

While the process can be conducted at a temperature as high as 325° C. the selectivity of desired products is such that a temperature in this range is not considered suitable. In order to have the desired selectivity the process suitably is conducted at a temperature of about 200° to about 295° C., preferably about 240° to about 280° C.

Usually the process is conducted at ambient pressure. However, a pressure as high as 100 psig can be used, if desired.

My process provides a high selectivity of orthomethylated phenolic products (i.e. o-cresol and 2,6-xylenol) in the product mixture. One selectivity parameter is the "R" value wherein R is defined as follows:

R = 2,6-xylenol/m,p-cresol ratio (weight ratio)

A means of expressing ortho-selectivity is the value "Sel(o+26)" wherein "Sel(o+26)" is defined as follows:

Sel(o+26) = combined selectivity of o-cresol + 2,6-xylenol

Using the foregoing definition my process will usually produce an "R" value of at least 18 and a "Sel(o+26)" value of at least 89. Preferably my process produces an "R" value of at least 30 and a "Sel(o+26)" value of at least 91.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example is comparative and shows the conversion of a feedstock over gamma-alumina in the absence of water. The feedstock had the following composition:

TABLE 1

| Feedstock - Example 1 | | | |
|---|---|---|---|
| Component | Weight (g) | w/o | Moles |
| Methoxybenzene | 108 | 21.70 | 1.0 |
| o-Methylmethoxybenzene | 61 | 12.26 | 0.5 |
| 2,6-Dimethylmethoxybenzene | 13.6 | 2.73 | 0.1 |
| Phenol | 207 | 41.60 | 2.2 |

TABLE 1-continued

| Feedstock - Example 1 | | | |
|---|---|---|---|
| Component | Weight (g) | w/o | Moles |
| o-Cresol | 108 | 21.70 | 1.0 |
| Total | 497.6 | 99.99 | 4.8 |

The gamma-alumina was prepared by calcining *CATAPAL ® alumina spheres at 650° C. for 2 hours. The alumina had a surface area of 193 m²/g and a crystallite size of 60 A°.

*CATAPAL ® alumina is described in U.S. Pat. No. 4,187,255, which patent is made a part of this disclosure.

The $\frac{\text{weight of feedstock per hour}}{\text{weight of catalyst}}$ was 1.30 hr$^{-1}$.

Process was conducted at 0 psig.

Runs were made at 300°, 325°, 350° and 375° C.

The results are shown in Table 2.

TABLE 2

| Results Obtained - Example 1 | | | | | |
|---|---|---|---|---|---|
| Run No. | Temp (°C.) | $R^a$ | Sel(o + 26)$^b$ (m/o) | % A Conv.$^c$ (w/o) | % OMA Conv. (w/o) | % DMA Conv.$^c$ (w/o) |
| A | 300 | 33.1 | 92.9 | 91.5 | 70.6 | 68.2 |
| B | 325 | 22.2 | 95.8 | 99.6 | 95.7 | 92.7 |
| C | 350 | 3.90 | 81.9 | 100 | 100 | 100 |
| D | 375 | 1.94 | 75.3 | 100 | 100 | 100 |

$^a$R = 2,6-xylenol/m,p-cresol ratio
$^b$Sel(o + 26) = selectivity (o-cresol + 2,6-xylenol) (mole %)
$^c$% A Conv. = percent anisole conversion.
% OMA Conv. = percent o-methylanisole conversion.
% DMA Conv. = percent 2,6-dimethylanisole conversion.

EXAMPLE 2

This example is illustrative and shows the results obtained when converting a feedstock, containing water, over gamma-alumina. The feedstock had the following composition:

TABLE 3

| Feedstock - Example 2 | | | |
|---|---|---|---|
| Component | weight (g) | (w/o) | Moles |
| Methoxybenzene | 108 | 21.34 | 1.0 |
| o-Methylmethoxybenzene | 61 | 12.05 | 0.5 |
| 2,6-Dimethylmethoxybenzene | 13.6 | 2.69 | 0.1 |
| Phenol | 207 | 40.91 | 2.2 |
| o-Cresol | 108 | 21.34 | 1.0 |
| Water | 8.45* | 1.67 | 0.47 |
| Total | 506.05 | 100 | 5.27 |

*1.67 weight percent of total

The gamma-alumina and amount used were the same as in Example 1.

Process was conducted at 0 psig.

Runs were made at 250°, 275°, 300° and 325° C.

The results are shown in Table 4.

TABLE 4

| Results Obtained - Example 2 | | | | | |
|---|---|---|---|---|---|
| Run No. | Temp (°C.) | $R^a$ | Sel (o + 26)$^b$ (m/o) | % A Conv.$^c$ (w/o) | % OMA Conv.$^c$ (w/o) | % DMA Conv.$^c$ (w/o) |
| E | 250 | 56.9 | 91.5 | 75.7 | 68.6 | 89.1 |
| F | 275 | 34.5 | 92.5 | 98.6 | 97.7 | 99.4 |
| G | 300 | 16.1 | 87.9 | 99.9 | 99.8 | 100 |
| H | 325 | 10.0 | 86.1 | 100 | 100 | 100 |

$^a$R = 2,6-xylenol/m,p-cresol ratio.
$^b$Sel(o + 26) = selectivity for o-cresol + 2,6-xylenol.
$^c$See footnote c of Table 2 for definitions of these terms.

Thus, having described the invention in detail, it will be understood by those skilled in the art that certain variations and modifications may be made without departing from the spirit and scope of the invention as defined herein and in the appended claims.

I claim:

1. A process for converting a feedstock comprising methoxybenzene, o-methylmethoxybenzene, 2,6-dimethylmethoxybenzene, or mixtures thereof, to a product mixture containing o-cresol and 2,6-xylenol in high selectivity, said process comprising passing the feedstock in vapor phase over an effective amount of gamma-alumina in the presence of an effective amount of water at a temperature in the range of about 225° to about 295° C., said process being characterized further in that the amount of water, based on the feedstock, is in the range of about 0.5 to about 10 weight percent.

2. The process of claim 1 wherein the amount of gamma-alumina, expressed as $$\frac{\text{weight of feedstock per hour}}{\text{weight of catalyst}}$$

is in the range of about 0.5 to about 2.5 hr$^{-1}$.

3. The process of claim 2 wherein the gamma-alumina is prepared by calcining alumina at a temperature in the range of about 470° to about 870° C. for at least 1 hour and has a surface area in the range of about 75 to about 350 m²/g.

4. The process of claim 1 wherein the reaction temperature is in the range of about 240° to about 280° C.

5. The process of claim 4 wherein the amount of water, based on the feedstock, is in the range of about 1 to about 4 percent by weight.

6. The process of claim 1 wherein the amount of gamma-alumina, expressed as $$\frac{\text{weight of feedstock per hour}}{\text{weight of catalyst}}$$

is in the range of about 0.8 to about 1.5 hr$^{-1}$.

7. The process of claim 6 wherein the gamma-alumina is prepared by calcining alumina at a temperature in the range of about 500° to about 650° C. and has a surface area in the range of about 150 to about 200 m²/g.

8. The process of claim 7 wherein the reaction temperature is in the range of about 240° to about 280° C.

9. The process of claims 2, 4, 5, or 8 wherein the amount of o-cresol and 2,6-xylenol in the product mixture is as follows:

R is at least 18 when R is expressed as R=2,6-xylenol/m,p-cresol ratio and Sel(o+26) is at least 89 where Sel(o+26)=selectivity of o-cresol+2,6-xylenol.

* * * * *